(12) United States Patent
Koch

(10) Patent No.: US 9,474,553 B2
(45) Date of Patent: Oct. 25, 2016

(54) CAPS FOR IMPLANTS, IMPLANT ASSEMBLIES, AND METHODS OF USE

(71) Applicant: DePuy Synthes Products, Inc., Raynham, MA (US)

(72) Inventor: Rudolf Koch, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 200 days.

(21) Appl. No.: 14/159,715

(22) Filed: Jan. 21, 2014

(65) Prior Publication Data

US 2014/0214096 A1 Jul. 31, 2014

Related U.S. Application Data

(60) Provisional application No. 61/756,758, filed on Jan. 25, 2013, provisional application No. 61/763,672, filed on Feb. 12, 2013.

(51) Int. Cl.

| | |
|---|---|
| *A61B 17/86* | (2006.01) |
| *A61B 17/68* | (2006.01) |
| *A61B 17/70* | (2006.01) |
| *A61C 7/10* | (2006.01) |
| *A61B 17/80* | (2006.01) |

(Continued)

(52) U.S. Cl.
CPC ......... *A61B 17/685* (2013.01); *A61B 17/7032* (2013.01); *A61B 17/8042* (2013.01); *A61B 17/823* (2013.01); *A61B 17/844* (2013.01); *A61C 7/10* (2013.01); *A61C 7/125* (2013.01); *A61C 8/00* (2013.01); *A61B 17/66* (2013.01); *A61B 17/82* (2013.01); *A61B 17/842* (2013.01); *A61B 2090/103* (2016.02); *A61F 2/30744* (2013.01)

(58) Field of Classification Search
CPC . A61B 17/8605; A61B 17/685; A61C 7/125
USPC .................. 606/301–331, 295, 74
See application file for complete search history.

(56) References Cited

U.S. PATENT DOCUMENTS

| | | | |
|---|---|---|---|
| 2,987,062 A | 6/1961 | Elllison | |
| 3,570,497 A | 3/1971 | Lemole | |

(Continued)

FOREIGN PATENT DOCUMENTS

| | | |
|---|---|---|
| DE | 3244680 | 6/1984 |
| DE | 3538645 | 5/1987 |

(Continued)

OTHER PUBLICATIONS

International Patent Application No. PCT/US2013/030681: International Search Report dated Jul. 5, 2013, 15 pages.

*Primary Examiner* — Christopher Beccia
(74) *Attorney, Agent, or Firm* — Baker & Hostetler LLP

(57) ABSTRACT

An implant assembly can include an implant configured to be coupled to at least one bone part. The implant can include an implant body that defines at least one unsmooth surface. The assembly can further include a cap configured to be coupled to the implant body such that the cap overlies the at least one unsmooth surface. The cap can include a shell that defines a cavity that is configured to receive at least a portion of the implant body such that the shell flexes relative to the implant body as the cavity receives the at least a portion of the implant body to thereby couple the cap to the implant. The cap defines an outer surface that is curved.

30 Claims, 12 Drawing Sheets

(51) Int. Cl.
    *A61C 7/12*         (2006.01)
    *A61C 8/00*         (2006.01)
    *A61F 2/30*           (2006.01)
    *A61B 17/66*          (2006.01)
    *A61B 17/82*          (2006.01)
    *A61B 17/84*          (2006.01)

(56) References Cited

U.S. PATENT DOCUMENTS

| | | |
|---|---|---|
| 3,577,601 A | 5/1971 | Mariani et al. |
| 3,835,860 A | 9/1974 | Garretson |
| 3,910,282 A | 10/1975 | Messer et al. |
| 4,037,603 A | 7/1977 | Wendorff |
| 4,119,091 A | 10/1978 | Partridge |
| 4,138,770 A | 2/1979 | Barrette et al. |
| 4,535,764 A | 8/1985 | Ebert |
| 4,730,615 A | 3/1988 | Sutherland et al. |
| 4,813,416 A | 3/1989 | Pollak et al. |
| 4,901,721 A | 2/1990 | Hakki |
| 4,955,913 A | 9/1990 | Robinson |
| 5,146,645 A | 9/1992 | Dirksing |
| 5,146,654 A | 9/1992 | Caveney et al. |
| 5,193,250 A | 3/1993 | Caveney |
| 5,318,566 A | 6/1994 | Miller |
| 5,355,913 A | 10/1994 | Green et al. |
| 5,356,417 A | 10/1994 | Golds |
| 5,366,461 A | 11/1994 | Blasnik |
| 5,383,882 A | 1/1995 | Buess et al. |
| 5,403,346 A | 4/1995 | Loeser |
| 5,437,685 A | 8/1995 | Blasnik |
| 5,456,246 A | 10/1995 | Schmieding et al. |
| 5,462,542 A | 10/1995 | Alesi, Jr. |
| 5,549,619 A | 8/1996 | Peters et al. |
| 5,636,412 A | 6/1997 | Lodi et al. |
| 5,766,218 A | 6/1998 | Arnott |
| 5,772,663 A | 6/1998 | Whiteside et al. |
| 5,879,371 A | 3/1999 | Gardiner et al. |
| 5,972,006 A | 10/1999 | Sciaino, Jr. |
| 5,972,024 A | 10/1999 | Northrup, III et al. |
| 6,049,949 A | 4/2000 | Guthke |
| 6,489,246 B1 | 12/2002 | Summa et al. |
| 6,589,246 B1 | 7/2003 | Hack et al. |
| 6,613,059 B2 | 9/2003 | Schaller et al. |
| 7,008,429 B2 | 3/2006 | Golobek |
| 7,164,360 B2 | 1/2007 | Schiebler |
| 7,582,089 B2 | 9/2009 | Schiebler |
| 7,648,504 B2 | 1/2010 | Heino et al. |
| 2003/0153947 A1 | 8/2003 | Koseki |
| 2003/0236538 A1 | 12/2003 | Aikens |
| 2004/0059357 A1 | 3/2004 | Koseki |
| 2004/0068292 A1 | 4/2004 | Koseki |
| 2005/0075667 A1 | 4/2005 | Schaller et al. |
| 2005/0090827 A1 | 4/2005 | Gedebou |
| 2005/0288674 A1 | 12/2005 | Golobek |
| 2006/0149390 A1 | 7/2006 | Long et al. |
| 2006/0276809 A1 | 12/2006 | Oliveira |
| 2007/0055258 A1 | 3/2007 | Hansen |
| 2007/0173934 A1 | 7/2007 | Dickinson et al. |
| 2007/0185488 A1 | 8/2007 | Pohjonen et al. |
| 2008/0249569 A1 | 10/2008 | Waugh et al. |
| 2009/0228022 A1 | 9/2009 | McClellan |
| 2009/0306716 A1 | 12/2009 | Berger et al. |
| 2009/0318962 A1 | 12/2009 | Spedden et al. |
| 2010/0274289 A1 | 10/2010 | Carls et al. |
| 2010/0292739 A1* | 11/2010 | Schwab ............ A61B 17/7032 606/305 |
| 2010/0298829 A1 | 11/2010 | Schaller et al. |
| 2011/0295257 A1 | 12/2011 | McClellan et al. |
| 2012/0041441 A1 | 2/2012 | Berstein et al. |
| 2012/0197256 A1 | 8/2012 | Knueppel |
| 2012/0221060 A1* | 8/2012 | Blain .................... A61B 17/82 606/279 |

FOREIGN PATENT DOCUMENTS

| | | |
|---|---|---|
| DE | 4021246 | 1/1992 |
| DE | 4024334 | 2/1992 |
| DE | 4200757 | 7/1992 |
| DE | 4127550 | 2/1993 |
| DE | 4314185 | 11/1993 |
| DE | 19716504 | 12/1998 |
| DE | 19806628 | 8/1999 |
| EP | 0009327 | 4/1980 |
| EP | 0201905 | 11/1986 |
| EP | 0238219 | 9/1987 |
| EP | 0299387 | 1/1989 |
| EP | 0512297 | 11/1992 |
| EP | 0597257 | 5/1994 |
| EP | 0608592 | 8/1994 |
| EP | 0780096 | 6/1997 |
| EP | 0813846 A1 | 12/1997 |
| EP | 0876798 | 11/1998 |
| EP | 0937930 | 8/1999 |
| EP | 1564144 | 8/2005 |
| FR | 2677536 | 12/1992 |
| FR | 2690727 | 11/1993 |
| FR | 2702951 | 9/1994 |
| FR | 2906704 | 4/2008 |
| GB | 2266557 | 11/1993 |
| GB | 2414936 | 12/2005 |
| JP | 2004-298501 | 10/2004 |
| WO | WO 88/06022 | 8/1988 |
| WO | WO 92/22041 | 12/1992 |
| WO | WO 97/16359 | 5/1997 |
| WO | WO 2005/062902 A2 | 7/2005 |
| WO | WO 2006/062419 | 6/2006 |
| WO | WO 2006/136938 | 12/2006 |
| WO | WO 2009/013397 | 1/2009 |
| WO | WO 2009/091313 | 7/2009 |
| WO | WO 2009/134424 A2 | 11/2009 |
| WO | WO 2010/041101 | 4/2010 |
| WO | WO 2010/108050 | 9/2010 |

* cited by examiner

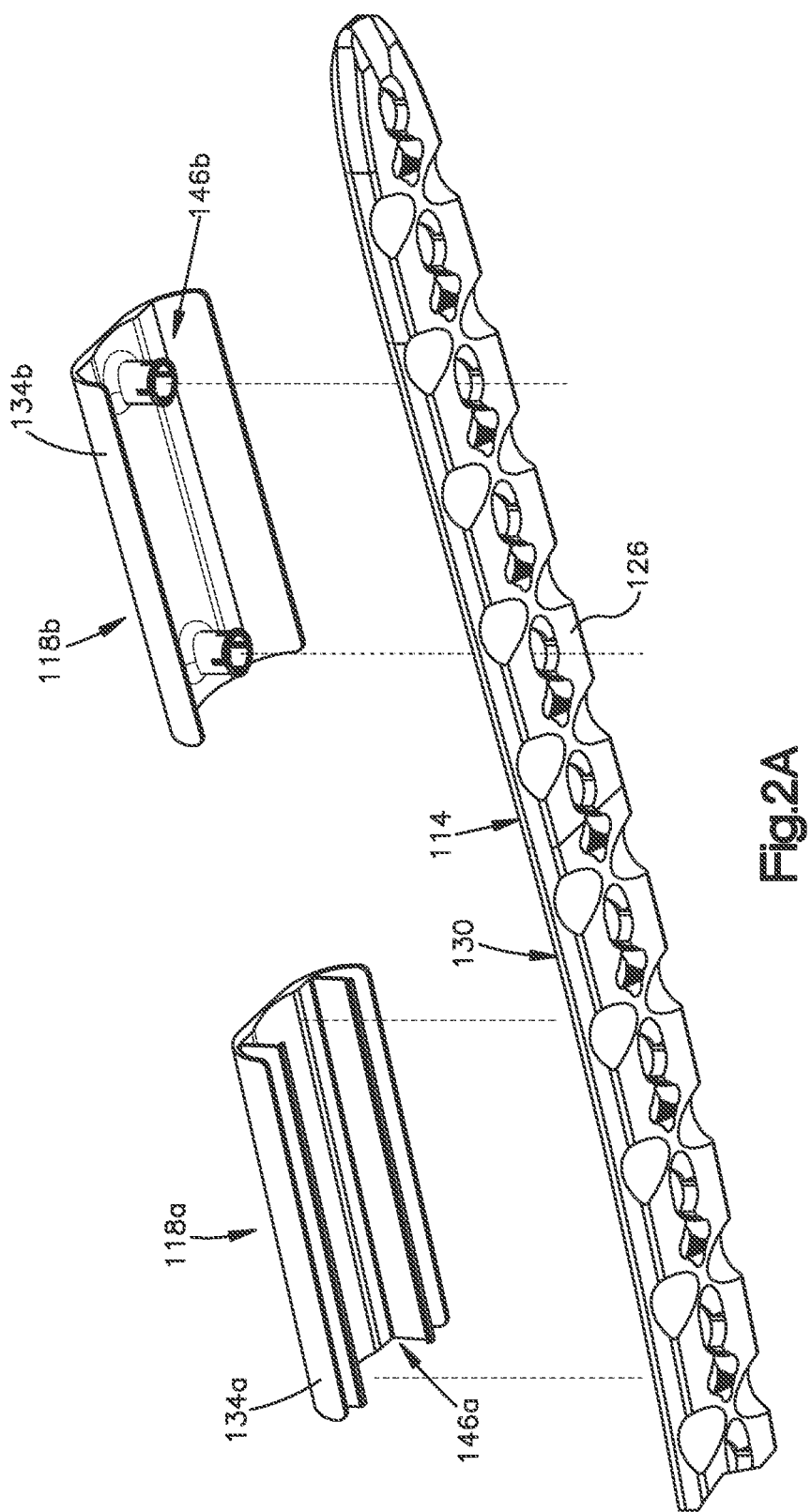

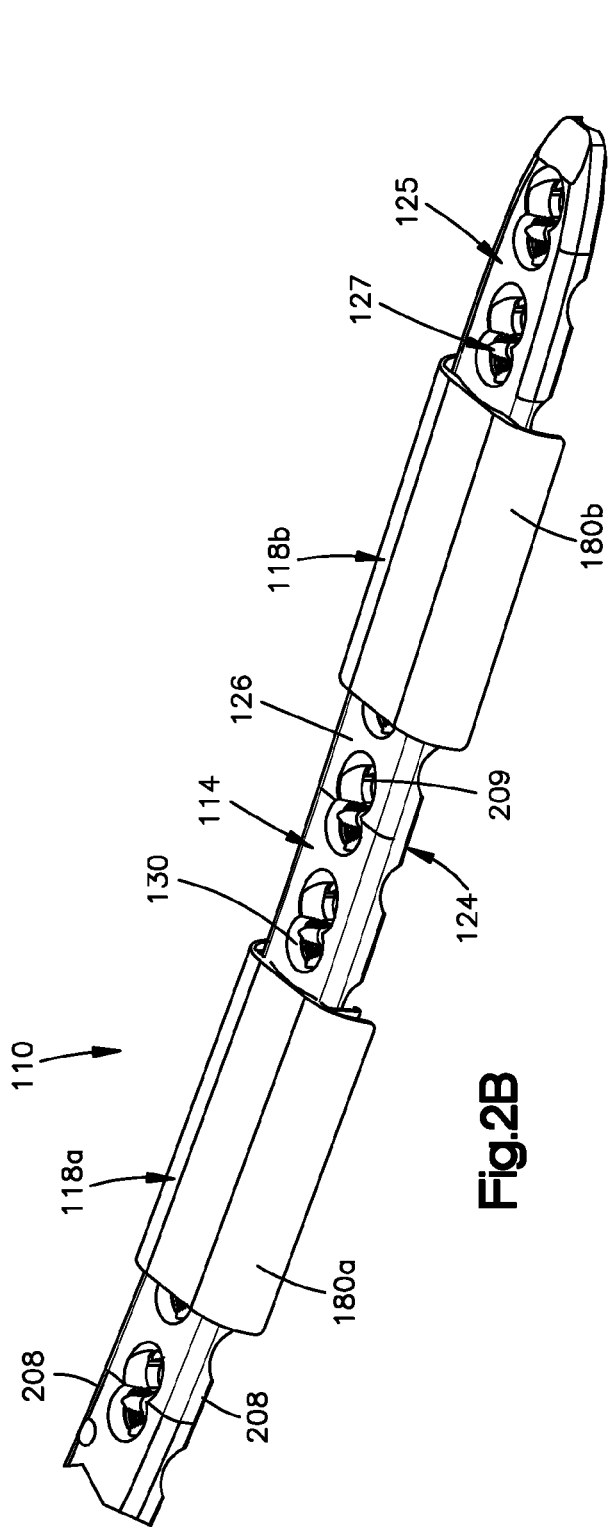
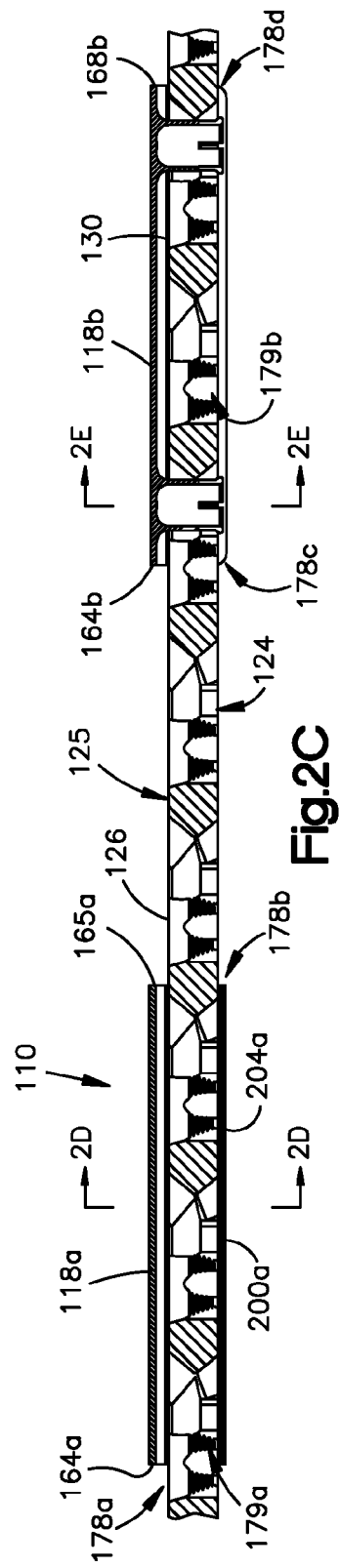
Fig.2B
Fig.2C

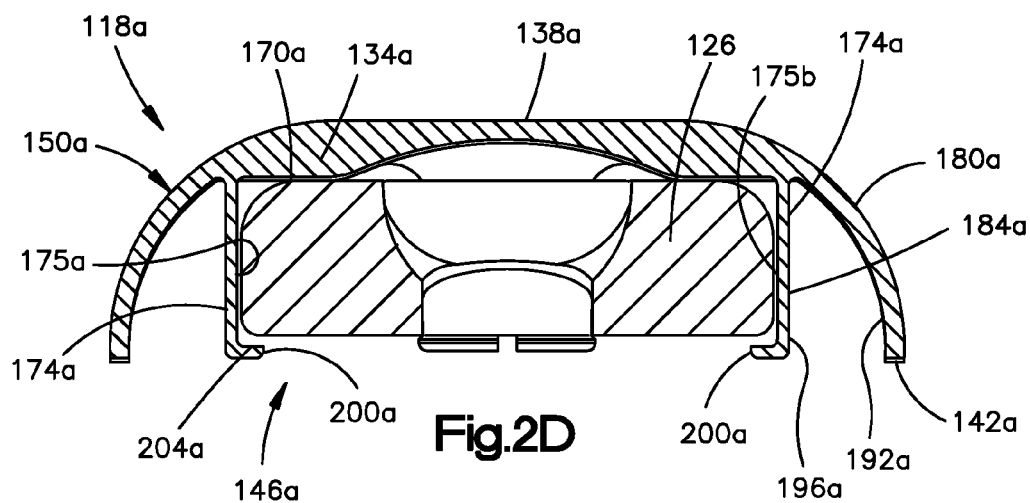
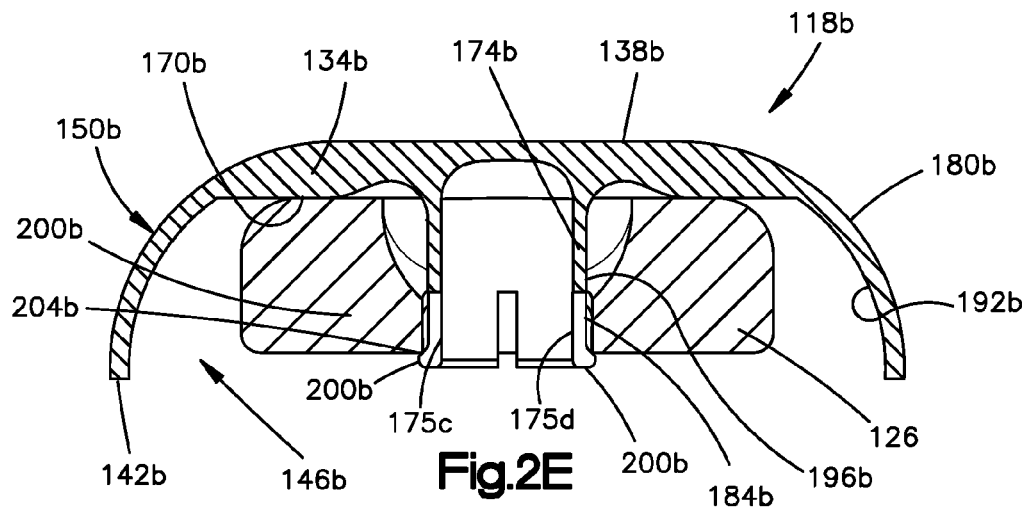

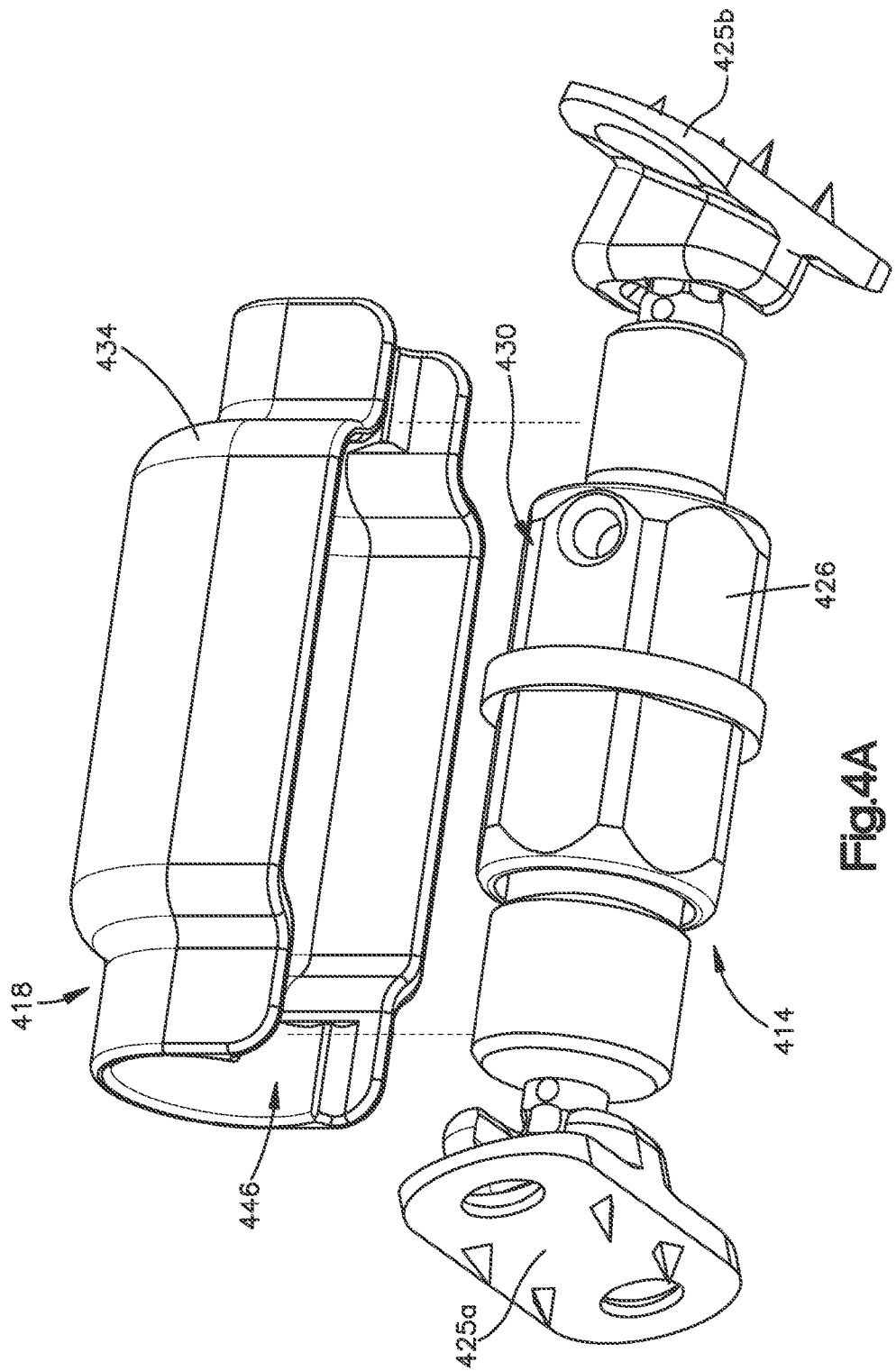

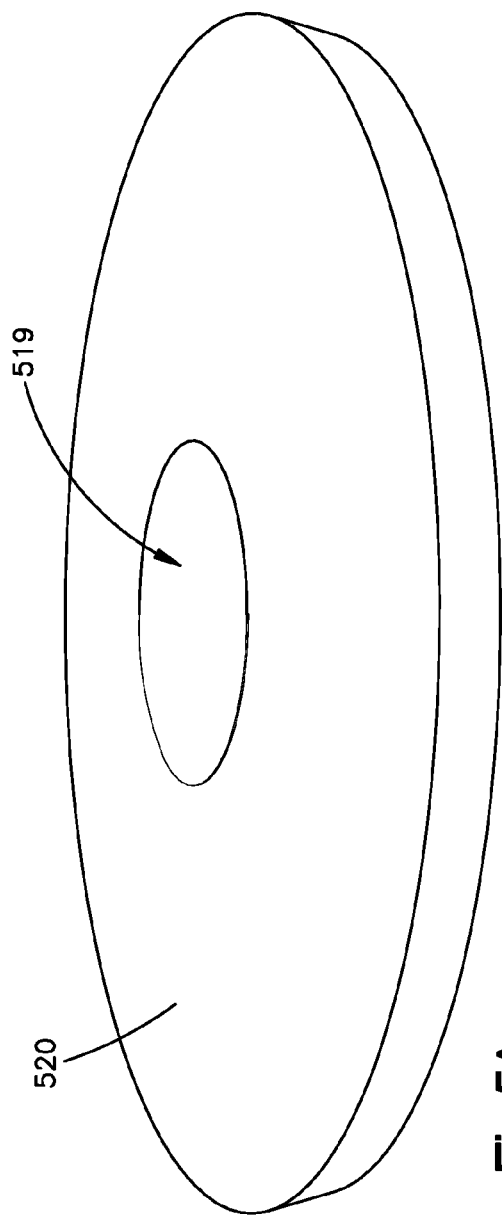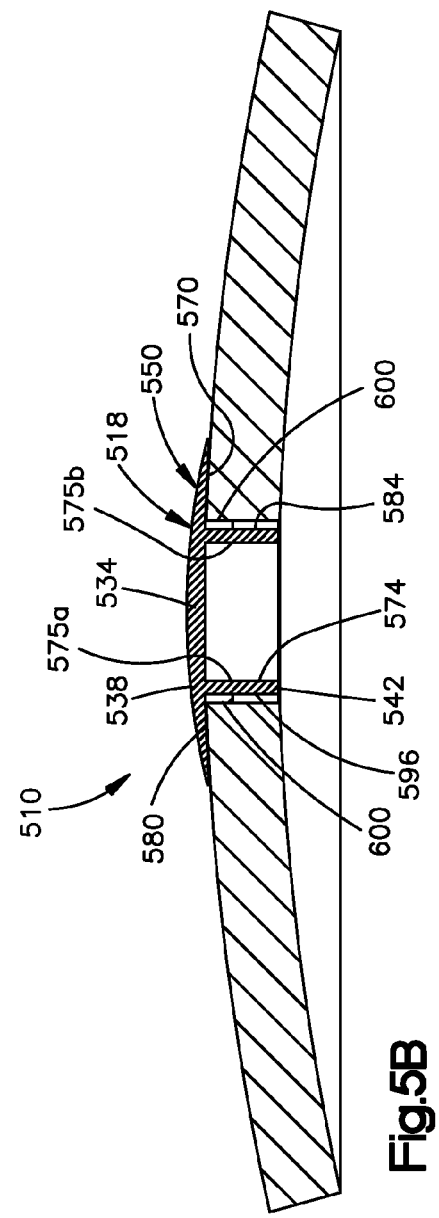

CAPS FOR IMPLANTS, IMPLANT ASSEMBLIES, AND METHODS OF USE

CROSS REFERENCE TO RELATED APPLICATIONS

This case claims priority to U.S. Provisional Application Ser. No. 61/756,758, filed Jan. 25, 2013 and to U.S. Provisional Application Ser. No. 61/763,672, filed Feb. 12, 2013, the contents of each of which is hereby incorporated by reference as if set forth in their entirety herein.

BACKGROUND

Medical procedures often times require the implantation of a device into a patient's body. For example, to fix two or more bones relative to each other, bone screws, bone plates, fixation members, or even distractors are coupled to the to two or more bones. Such devices or implants typically have sharp edges that can cause irritation to the surrounding soft tissue such as for example to the surrounding blood vessels, muscles including the tongue, nerves, skin and dura.

SUMMARY

In an embodiment, a cap can be configured to be coupled to an implant having an implant body. The cap can include a cap body that includes a shell having at least one side wall that defines at least a first inner surface and a second inner surface that is spaced from the first inner surface along a first direction. The first and second inner surfaces can at least partially define a cavity that is sized to receive at least a portion of the implant body such that the shell flexes between a first position and a second position as the cavity receives the at least a portion of the implant body. The cap can further include an attachment mechanism that is configured to abut an inner surface of the implant when the shell is in the second position to thereby trap the at least a portion of the implant body within the cavity.

In another embodiment, an implant assembly can include an implant configured to be coupled to at least one bone part. The implant can include an implant body that defines at least one unsmooth surface. The assembly can further include a cap configured to be coupled to the implant body such that the cap overlies the at least one unsmooth surface. The cap can include a shell that defines a cavity that is configured to receive at least a portion of the implant body such that the shell flexes relative to the implant body as the cavity receives the at least a portion of the implant body to thereby couple the cap to the implant. The cap defines an outer surface that is curved.

In another embodiment, a method of fixing a first bone part relative to a second bone part can include the steps of fixing a first bone part relative to a second bone part with an implant that defines a bone facing surface and an opposed outer surface; positioning a cap defining a curved outer surface over the outer surface of the implant, the cap having a shell that defines a cavity, the cap further having at least one attachment member that extends from the shell; and moving the cap toward the implant such that the cavity receives a portion of the implant and until the at least one attachment member abuts the bone facing surface to thereby couple the cap to the implant.

BRIEF DESCRIPTION OF THE DRAWINGS

The foregoing summary, as well as the following detailed description of the preferred embodiments of the application, will be better understood when read in conjunction with the appended drawings. For the purposes of illustrating the present disclosure, there is shown in the drawings preferred embodiments. It should be understood, however, that the application is not limited to the specific embodiments and methods disclosed, and reference is made to the claims for that purpose. In the drawings:

FIG. 2A is a perspective exploded view of an implant assembly that includes a bone plate and a pair of caps constructed in accordance with another embodiment, the pair of caps being configured to couple to the bone plate, such that each cap overlies the bone plate so as to reduce sharp edges or otherwise provide smoother edges for the bone plate;

FIG. 2B is a top perspective view of the caps shown in FIG. 2A coupled to the bone plate;

FIG. 2C is a side sectional view of the pair of caps shown in FIG. 2B coupled to the bone plate;

FIG. 2D is a cross-sectional view of a first cap of the pair of caps shown in FIG. 2B through the line 2D-2D, the first cap having a pair of attachment members that couple to the sides of the bone plate;

FIG. 2E is a cross-sectional view of the a second cap of the pair of caps shown in FIG. 2B through the line 2E-2E, the second cap having a pair of attachment members that couple to the bone fixation holes of the bone plate;

FIG. 4A is a perspective exploded view of an implant assembly that includes a distractor and a cap constructed in accordance with another embodiment, the cap being configured to couple to a body of the distractor, such that the cap overlies the body so as to reduce sharp edges or otherwise provide smoother edges for the body of the distractor;

FIG. 5A is a top perspective view of an implant assembly that includes a cap constructed in accordance with another embodiment, the cap coupled to an aperture in a clamp member of a cranial clamp, the cap being configured to overlie the clamp member so as to reduce sharp edges or otherwise provide smoother edges for the clamp member; and FIG. 5B is a cross-sectional view of the cap shown in FIG. 5A coupled to the clamp member through the line 5B-5B.

DETAILED DESCRIPTION OF ILLUSTRATIVE EMBODIMENTS

Figure 1A:
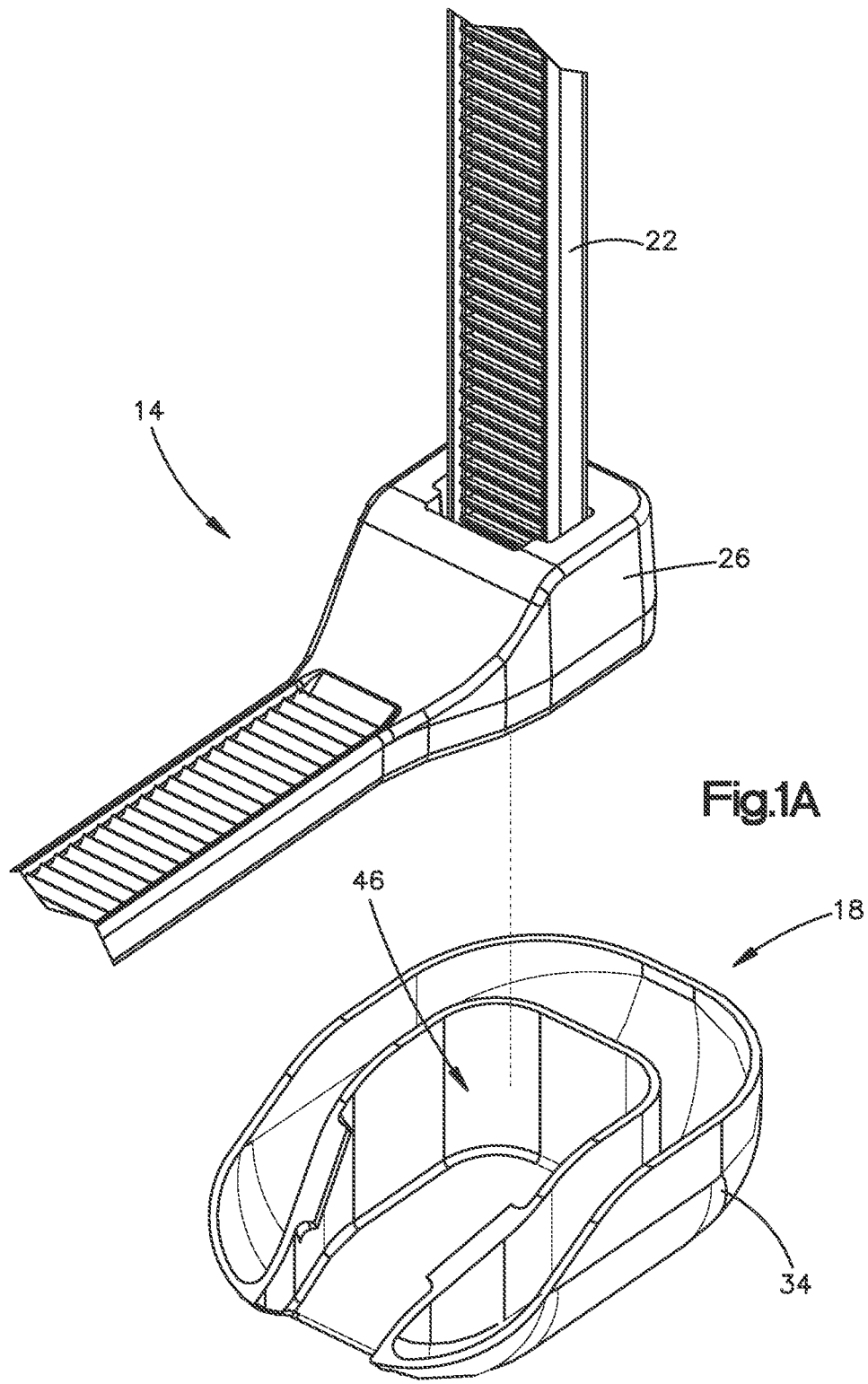
FIG. 1A is a perspective exploded view of an implant assembly that includes a bone fixation member and a cap constructed in accordance with an embodiment, the cap being configured to couple to a locking head of the bone fixation member, such that the cap overlies the locking head so as to reduce sharp edges or otherwise provide smoother edges for the bone fixation member.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical instrument. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Figure 1B:
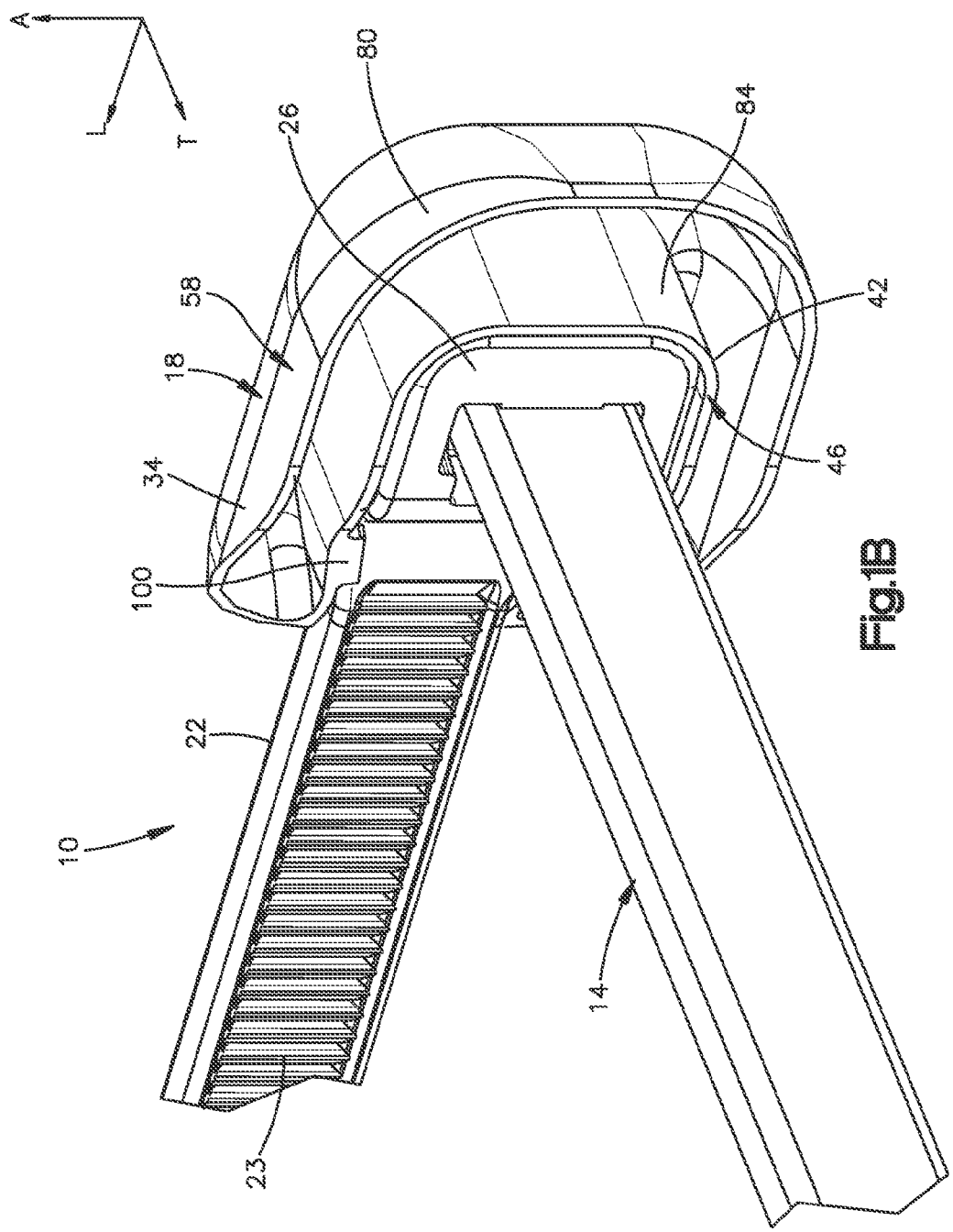
FIG. 1B is a bottom perspective view of the cap shown in FIG. 1A coupled to the locking head.

Referring to FIGS. 1A-1D an implant assembly 10 can include an implant, illustrated as a bone fixation member 14 that is configured to be coupled to at least one bone part and a cap 18 that is configured to be coupled to the bone fixation member 14. In particular, the bone fixation member 14 is configured to secure first and second bone parts of a target bone, such as a sternum, that are separated at a fracture location together in a compressed approximated position. As shown in FIGS. 1A and 1B, the bone fixation member 14 can be substantially configured as a cable tie, and extends horizontally along a longitudinal direction L and a lateral direction A, and vertically along a transverse direction T. The bone fixation member 14 includes a flexible strap 22 that is elongate along the longitudinal direction and an implant body that is configured as a locking head 26 that extends from an end of the strap 22 along the longitudinal direction L.

The locking head can define an inner surface 24 such as a bone facing surface, an outer surface 25, a slot 27 that extends through the locking head 26 from the bone facing surface 24 to the outer surface 25. The locking head can further include at least one locking tooth 28 that extends into the slot 27. The strap 22 can define a plurality of teeth 23 that are configured to engage the at least one tooth 28 of the locking head 26 as the strap 22 translates through the slot 27. The implant body or locking head 26 can be substantially box shaped so as to define at least one unsmooth surface 30. For example, because the locking head 26 is substantially box shaped, edges of the locking head can be sharp or otherwise non-rounded. Therefore, it can be said that the locking head 26 has at least one unsmooth surface 30. In the illustrated embodiment, the bone facing surface 24 is the bottom surface of the locking head 26 and the at least one unsmooth surface 30 of the locking head 26 is the top surface. It should be appreciated, however, that the bone facing surface 24 can be any surface that faces the bone and that the at least one unsmooth surface 30 can be any surface on the locking head 26. Further, it should be appreciated, that an unsmooth surface 30 can be any surface that is segmented, or otherwise interrupted, any surface that includes sharp edges, or any surface that includes a protuberance, for example.

With continued reference to FIGS. 1A-1D, the cap 18 can be configured to be coupled to the locking head 26, such that the cap 18 overlies the locking head or at least the unsmooth surface 30 to thereby eliminate the unsmooth surface and/or reduce the palpability of the locking head 26. Therefore, the cap 18 can be configured to remove sharp edges from and/or reduce the palpability of the locking head 26 when coupled to the locking head 26. As shown in FIGS. 1A and 1B the cap 18 includes a cap body 34 that is curved or otherwise rounded so as to reduce irritation that may be caused to the surrounding soft tissue by the locking head 26. The cap body 34 defines a first or upper end 38 and a second or lower end 42 that is spaced from the first end 38 along the transverse direction. The cap body 34 further includes a cavity 46 that extends into the lower end 42. The cavity 46 is configured to receive at least a portion of, such as a major portion of the locking head 26. It should be appreciated, however, that the cavity 46 can be configured to receive any locking head, as desired.

Figure 1C:
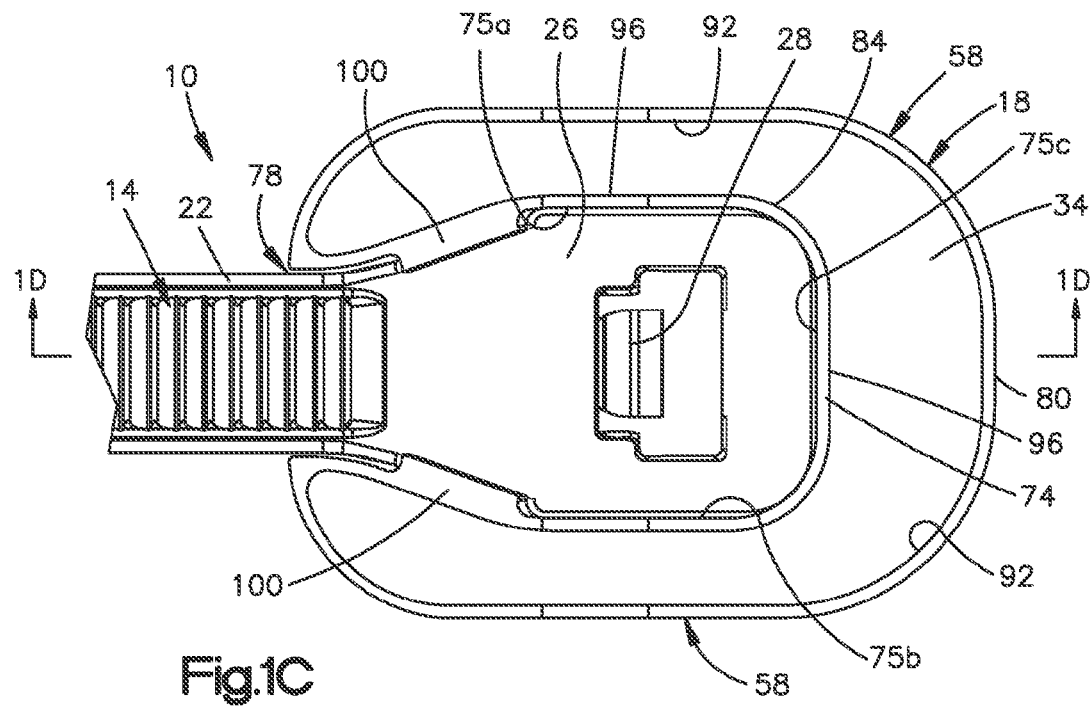
FIG. 1C is a bottom plan view of the implant assembly shown in FIG. 1B.
Figure 1D:
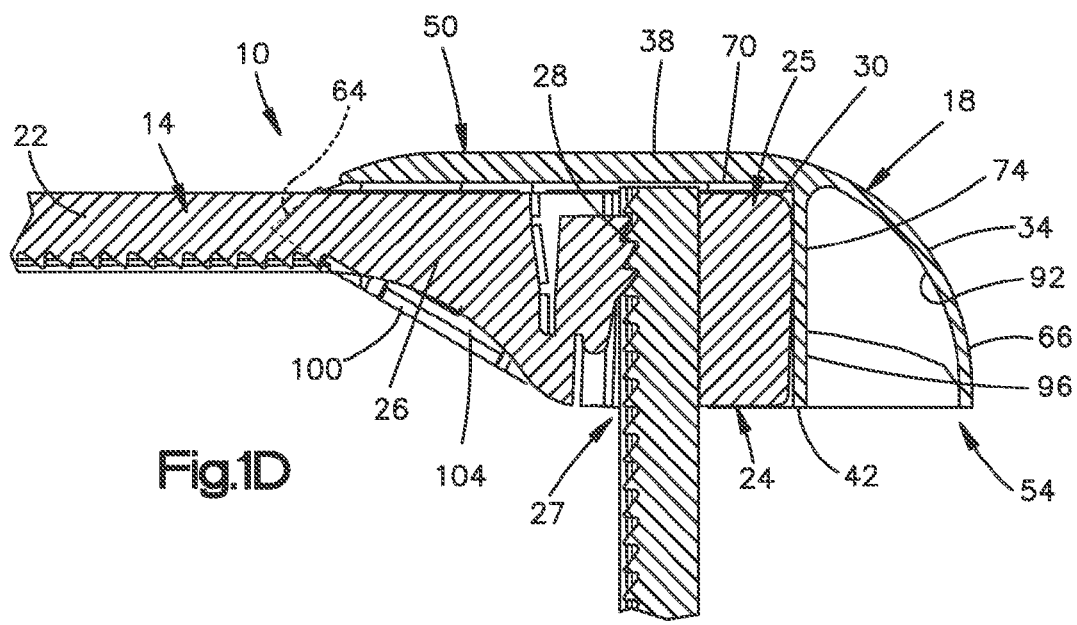
FIG. 1D is a cross-sectional view of the cap shown in FIG. 1C coupled to the locking head through the line 1D-1D.

As shown in FIG. 1C, the first end 38 of the cap body 34 defines an upper surface 50 and the second end 42 of the cap body 34 defines a lower surface 54. The cap body 34 further defines two opposed side surfaces 58 that merge into the upper and lower surfaces 50 and 54. As shown, the cap body 34 is curved, or otherwise rounded along the longitudinal direction L and includes a distal body end 64 and a proximal body end 68 spaced from the distal body end 64 along the longitudinal direction L. The cap body 34 can be curved from a location between the distal and proximal body ends 64 and 68 to the proximal body end 68. Therefore, the upper surface 50 is substantially convex along the longitudinal direction L. As shown in FIG. 1D, the upper surface 50 is curved such that the slope of the upper surface 50 increases as the upper surface 50 extends toward the proximal body end 68.

As shown in FIGS. 1B-1D, the cap body 34 can define an outer shell 80 and an inner shell 84 disposed within the outer shell 80. The inner shell 84 includes a ceiling 70 and at least one side wall 74 that extends down from the first end 38 and defines at least a first inner surface 75a and a second inner surface 75b that is spaced from and substantially faces the first inner surface 75a along a first direction (e.g. the lateral direction) such that the ceiling 70 and the first and second inner surfaces 75a and 75b at least partially define the cavity 46. In the illustrated embodiment, the at least one side wall 74 defines a third surface 75c that joins the first surface 75a to the second surface 75b such that the first, second, and third surfaces 75a-75c are continuous. It should be appreciated, however, that the inner shell 84 can include three side walls that each defines the respective inner surfaces 75a-75c. It should also be appreciated, that the second inner surface 75b can face the first inner surface 75a such that a line that is orthogonal to the second inner surface 75a extends toward the first inner surface or at least has a directional component that extends toward the first inner surface. Therefore, the first and second inner surfaces 75a and 75b can define planes that are parallel to each other or can define planes that are oblique to each other and still substantially face each other.

As shown in FIG. 1D, the distal end of the cap body 34 defines an opening 78 that extends into the cavity 46. The ceiling 70 and the at least one side wall 74 are configured to cover the locking head 26 when the locking head 26 is received within the cavity 46, and the opening 78 is configured to allow the strap 22 to extend through the opening 78 when the locking head 26 is received within the cavity 46.

As shown in FIG. 1C, the outer shell 80 can define an inner surface 92 and the inner shell 84 can further define an outer surface 96 that faces and is spaced apart from the inner surface 92 along at least a portion of the surfaces 92 and 96. Because inner and outer surfaces 92 and 96 of the outer and inner shells 80 and 84, respectively, are spaced from each other, the inner shell 84 is configured to elastically flex relative to the outer shell 80 as the cavity 46 receives the locking head 26. That is, the side walls 74 of the inner shell 84 are configured to elastically flex outwardly between a first position and a second position as the cavity 46 receives the locking head 26. It should be appreciated, however, that the inner shell 84 can be configured to be non-flexible. Moreover, it should be appreciated, that the cap body 34 can be void of the inner shell 84 and can define an outer shell that defines the cavity 46.

With continued reference to FIGS. 1B-1D, the cap 18 can further include an attachment mechanism that is configured to couple the cap 18 to the locking head 26. In the illustrated embodiment, the attachment mechanism includes at least one, such as a first and a second attachment member 100 that are configured to couple the cap 18 to the locking head 26. As shown, the attachment mechanism or each attachment member 100 can be defined by or otherwise extend from the at least one side wall 74 substantially along the first direction. In the illustrated embodiment, the first and second attachment members 100 extend toward each other into the cavity 46 from a location that is proximate to the lower end 32 and are opposed to each other along the first direction. The attachment members 100 can each define an abutment surface 104 that faces the ceiling 70 of the cavity 36 such that when the cap 18 is coupled to the locking head 26 the abutment surfaces 104 abut the bone facing surfaces 24 of the locking head 26 to thereby trap or otherwise secure the locking head within the cavity 46. It should be appreciated, that the attachment members can include other configurations. For example, the attachment members 100 can define C-clips. Moreover, it should be appreciated that the cap 18 can include features other than the attachment members 100 that are configured to couple the cap 18 to the locking head 26. For example, the attachment mechanism can be a surface of the at least one side wall 74 such that the surface creates a frictional fit with the locking head or the attachment mechanism can be a fixation member such as a needle. Even further, the first and second attachment members 100 can be configured to abut respective bone facing surfaces of the locking head.

In operation, a bone fixation members 14 may be placed about the bone segments and of the sternum between adjacent ribs and the strap 22 can be pulled through the slot 27. As the strap 22 is translated through the slot 27 of the locking head 26 the locking teeth 28 and 23 can engage to prevent the tension that is induced in the strap 22 from causing the strap 22 to back out of the slot 27. Once the strap 22 has reached a maximum desired tension, the free end of the bone fixation member 14 can be cut off. After the free end is removed, the cap 18 can be coupled to the locking head 26 to thereby smooth out the sharp edges of the locking head 26.

In another embodiment and in reference to FIGS. 2A-2E, an implant assembly 110 can include an implant, illustrated as a bone plate 114 that is configured to be coupled to at least one bone part, a first cap 118a and/or a second cap 118b that are both configured to be coupled to the bone plate 114. In particular, the bone plate 114 is configured to secure first and second bone parts that are separated at a fracture location together in a compressed approximated position. The bone plate 114 can include a plate body 126 that defines an inner surface 124 such as a bone facing surface, an opposed outer surface 125, and a plurality of bone fixation apertures 127 that extend through the plate body 126 from the bone facing surface 124 to the outer surface 125. The plate body 126 can further include at least one bone fixation element that extends through one of the bone fixation apertures 127 and into one of the bone parts to thereby couple the bone plate 114 to the bone part. The plate body 126 can be substantially box shaped so as to define at least one unsmooth surface 130. For example, because the plate body 126 is substantially box shaped, edges of the plate body 126 can be sharp or otherwise non-rounded. Therefore, it can be said that the plate body 126 has at least one unsmooth surface 130. Further, the bone fixation element that extends through one of the bone fixation apertures 127 can also define the at least one unsmooth surface 130.

With continued reference to FIGS. 2A-2D, the cap 118a can be configured to be coupled to the plate body 126, such that the cap 118a overlies the plate body 126 or at least the unsmooth surface 130 to thereby eliminate the unsmooth surface and/or reduce the palpability of the plate body 126. Therefore, the cap 118a can be configured to remove sharp edges from and/or reduce the palpability of the plate body 126 when coupled to the plate body 126. As shown in FIG. 2A the cap 118a includes a cap body 134a that is curved or otherwise rounded so as to reduce irritation that may be caused to the surrounding soft tissue by the plate body 126. The cap body 134a defines a first or upper end 138a and a second or lower end 142a that is spaced from the first end 138a along the transverse direction. The cap body 134a further includes a cavity 146a that extends into the lower end 142a. The cavity 146a is configured to receive at least a portion of the plate body 126.

As shown in FIG. 2D, the first end 138a of the cap body 134a defines an upper surface 150a that is curved, or otherwise rounded along the lateral direction A and includes a distal body end 164a and a proximal body end 168a spaced from the distal body end 164a along the longitudinal direction L. The cap body 134a can be curved along the lateral direction so as to define a convex outer surface 150a. As shown in FIG. 2D, the upper surface 150a is curved such that the slope of the upper surface 150a increases as the upper surface 150a extends laterally in opposite directions from a centerline of the upper surface 150a.

As shown in FIGS. 2B-2D, the cap body 134a can define an outer shell 180a and an inner shell 184a disposed within the outer shell 180a. The inner shell 184a includes a ceiling 170a and at least two side walls 174a that extend down from the first end 138a and define at least a first inner surface 175a and a second inner surface 175b that is spaced from and substantially faces the first inner surface 175a along a first direction (e.g. the lateral direction) such that the ceiling 170a and the first and second inner surfaces 175a and 175b at least partially define the cavity 146a. In the illustrated embodiment, the inner shell 184a includes a first side wall 174a and a second side wall 174a that is spaced from the first side wall 174a such that the first inner surface 175a is parallel to the second inner surface 175b. Further, in the illustrated embodiment, the ceiling 170a defines a recess 171 that is configured to receive a portion of a bone fixation element head when the cap 118a is coupled to the implant body 126 over the bone fixation element.

As shown in FIG. 2C, the distal end of the cap body 134a defines a first opening 178a that extends into the cavity 146a and the proximal end of the cap body 134a defines a second opening 178b that extends into the cavity 146a. The cavity 146a and the first and second openings 178a and 178b together define a channel 179a that extends through the cap body 134*a* along a second direction (e.g. the longitudinal direction) that is substantially perpendicular to the first direction. The channel 179*a* is configured to receive the plate body so as to cover a portion of the plate body 126 and the openings 178*a* and 178*b* are configured to allow the plate body 126 to extend through the openings 178*a* and 178*b* when the portion of the plate body 126 is received within the cavity 146*a* or channel 179*a*. It should be appreciated, that while the first and second side walls 174*a* are each continuous along the second direction, the first and second side walls 174*a* can be segmented along the second direction, as desired.

As shown in FIG. 2D, the outer shell 180*a* can define an inner surface 192*a* and the inner shell 184*a* can further define an outer surface 196*a* that faces and is spaced apart from the inner surface 192*a* along at least a portion of the surfaces 192*a* and 196*a*. Because inner and outer surfaces 192*a* and 196*a* of the outer and inner shells 180*a* and 184*a*, respectively, are spaced from each other, the inner shell 184*a* is configured to elastically flex relative to the outer shell 180*a* as the cavity 146*a* receives the plate body 126. That is, the side walls 174*a* of the inner shell 184*a* are configured to elastically flex outwardly between a first position and a second position as the cavity 146*a* receives the plate body 126. It should be appreciated, however, that the inner shell 184*a* can be configured to be non-flexible. Moreover, it should be appreciated, that the cap body 134*a* can be configured such that the outer shell defines the cavity 146*a*.

With continued reference to FIG. 2D, the cap 118*a* can further include an attachment mechanism that is configured to couple the cap 118*a* to the body 126. In the illustrated embodiment, the attachment mechanism includes at least one, such as a first and a second attachment member 200*a* that are each configured to capture the cap 118*a* to the body 126. As shown, the attachment mechanism or each attachment member 200*a* can be defined by or otherwise extend from the at least one side wall, such as from each of the first and second side walls 174*a* substantially along the first direction. In the illustrated embodiment, the first and second attachment members 200*a* extend toward each other into the cavity 146*a* from a location that is proximate to the lower end 142*a* and are opposed to each other along the first direction. The attachment members 200*a* can each define an abutment surface 204*a* that faces the ceiling 170*a* of the cavity 146*a* such that when the cap 118*a* is coupled to the plate body 126 the abutment surfaces 204*a* abut the bone facing surface(s) 124 of the plate body 126 to thereby trap or otherwise secure the plate body 126 within the cavity 146*a*. It should be appreciated, that the attachment members can include other configurations. For example, the attachment members 200*a* can define C-clips. Moreover, it should be appreciated that the cap 118*a* can include features other than the attachment members 200*a* that are configured to couple the cap 118*a* to the plate body 126. For example, the attachment mechanism can be respective surfaces of the side walls 174*a* such that the surfaces create a frictional fit with the body.

In the illustrated embodiment, the first and second side walls 174*a* are spaced from each other such that the first and second inner surfaces 175*a* and 175*b* abut outer side surfaces 208 of the implant body 126 when the cap 118*a* is coupled to the implant body 126. In operation, a plate 114 may be placed on at least two bone parts and secured to the bone parts with respective bone fixation elements. The cap 118*a* can then be coupled to the plate body 126 to thereby smooth out the sharp edges of the plate body 126. The cap 118*a* can be coupled to the implant body 126 such that the cap 118*a* overlies the bone fixation element of the implant body 126 or over a portion of the implant body 126 between adjacent bone fixation element receiving apertures.

Now in reference to FIGS. 2A, 2B, 2C, and 2E, the cap 118*b* can be configured to be coupled to the plate body 126 through one of the bone fixation apertures 127, such that the cap 118*b* overlies the plate body 126 or at least the unsmooth surface 130 to thereby eliminate the unsmooth surface and/or reduce the palpability of the plate body 126. Therefore, the cap 118*b* can be configured to remove sharp edges from and/or reduce the palpability of the plate body 126 when coupled to the plate body 126. As shown in FIGS. 2A and 2B the cap 118*b* includes a cap body 134*b* that is curved or otherwise rounded so as to reduce irritation that may be caused to the surrounding soft tissue by the plate body 126. The cap body 134*b* defines a first or upper end 138*b* and a second or lower end 142*b* that is spaced from the first end 138*b* along the transverse direction. The cap body 134*b* further includes a cavity 146*b* that extends into the lower end 142*b*. The cavity 146*b* is configured to receive at least a portion of the plate body 126.

As shown in FIG. 2E, the first end 138*b* of the cap body 134*b* defines an upper surface 150*b* that is curved, or otherwise rounded along the lateral direction A and includes a distal body end 164*b* and a proximal body end 168*b* spaced from the distal body end 164*b* along the longitudinal direction L. The cap body 134*b* can be curved along the lateral direction so as to define a convex outer surface 150*b*. As shown in FIG. 2E, the upper surface 150*b* is curved such that the slope of the upper surface 150*b* increases as the upper surface 150*b* extends laterally in opposite directions from a centerline of the upper surface 150*b*.

As shown in FIGS. 2A-2C and 2E, the cap body 134*b* can define an outer shell 180*b* and an inner shell 184*b* disposed within the outer shell 180*b*. The outer shell 184*b* includes a ceiling 170*b* and the inner shell 184*b* includes at least one side wall 174*b* that define at least a first inner surface 175*c* and a second inner surface 175*d* that is spaced from and substantially faces the first inner surface 175*c* along a first direction (e.g. the lateral direction). As shown in FIG. 2D, the outer shell 180*b* can define first and second inner surfaces 192*b* and the inner shell 184*b* can further define first and second outer surfaces 196*b* that face and are spaced apart from the inner surfaces 192*b* along at least a portion of the surfaces 192*a* and 196*a*. The ceiling 170*b*, inner surface 192*b* and outer surface 196*b* at least partially define the cavity 146*b*. Because inner and outer surfaces 192*b* and 196*b* of the outer and inner shells 180*b* and 184*b*, respectively, are spaced from each other, the inner shell 184*b* is configured to elastically flex relative to the outer shell 180*b* as the cavity 146*b* receives the plate body 126. That is, the at least one side wall 174*b* of the inner shell 184*b* is configured to elastically flex inwardly between a first position and a second position as the cavity 146*b* receives the plate body 126. It should be appreciated, however, that the inner shell 184*a* can be configured to be non-flexible, as desired.

The inner shell 184*b* or at least the at least one side wall 174*b* can be configured to be inserted through one of the bone fixation apertures 127 of the plate body 126. In the illustrated embodiment, the at least one side wall 174*b* is substantially continuous and is substantially cylindrical in shape. It should be appreciated, however, that the at least one side wall 174*b* is discontinuous and/or has a different shape as desired, so long as the inner shell 184*b* can be passed through one of the bone fixation apertures 127.

As shown in FIG. 2C, the distal end of the cap body 134b defines a first opening 178c that extends into the cavity 146b and the proximal end of the cap body 134b defines a second opening 178d that extends into the cavity 146b. The cavity 146b and the first and second openings 178c and 178d together define a channel 179b that extends through the cap body 134b along a second direction (e.g. the longitudinal direction) that is substantially perpendicular to the first direction. The channel 179b is configured to receive the plate body so as to cover a portion of the plate body 126 and the openings 178c and 178d are configured to allow the plate body 126 to extend through the openings 178c and 178d when the portion of the plate body 126 is received within the cavity 146b or channel 179b.

With continued reference to FIG. 2E, the cap 118b can further include an attachment mechanism that is configured to couple the cap 118b to the body 126. In the illustrated embodiment, the attachment mechanism includes at least one, such as a first and a second attachment member 200b that are configured to couple the cap 118b to the body 126. As shown, the attachment mechanism or each attachment member 200b can be defined by or otherwise extend from the at least one side wall substantially along the first direction. In the illustrated embodiment, the first and second attachment members 200b extend away from each other into the cavity 146b from a location that is proximate to the lower end 142b and are opposed to each other along the first direction. The attachment members 200b can each define an abutment surface 204b that faces the ceiling 170b of the cavity 146b such that when the cap 118b is coupled to the plate body 126 the abutment surfaces 204b abut the bone facing surface(s) 124 of the plate body 126 to thereby trap or otherwise secure the plate body 126 within the cavity 146b. The first and second attachment members 200b can extend around the side wall so as to define a continuous attachment member. Further the attachment member 200b can be opposed along any direction as desired. It should be appreciated, that the attachment members can include other configurations. For example, the attachment members 200b can define C-clips. Moreover, it should be appreciated that the cap 118b can include features other than the attachment members 200b that are configured to couple the cap 118b to the plate body 126. For example, the attachment mechanism can be respective surfaces of the side walls 174b such that the surfaces create a frictional fit with the body or the attachment mechanism can be a fixation member such as a needle. Even further, the first and second attachment members 200b can be configured to abut respective bone facing surfaces of the plate body.

In the illustrated embodiment, and in continued reference to FIG. 2E, the at least one side wall 174b is configured such that the outer surface abuts inner surfaces 209 of the implant body 126 that define the bone fixation apertures 127 when the cap 118b is coupled to the implant body 126. In operation, a plate 114 may be placed on at least two bone parts and secured to the bone parts with respective bone fixation elements. The cap 118b can then be coupled to the plate body 126 to thereby smooth out the sharp edges of the plate body 126. The cap 118b can be coupled to the implant body 126 such that the cap 118b overlies the bone fixation element aperture with or without a bone fixation element of the implant body 126 or over a portion of the implant body 126 between adjacent bone fixation element receiving apertures.

In another embodiment and in reference to FIGS. 3A-3D, an implant assembly 310 can include an implant, illustrated as a bone fixation element, such as a pedicle screw and fixation rod system 314 that is configured to be coupled to at least one vertebra and a cap 318 is configured to be coupled to the system 314. In particular, the system 314 is configured to secure first and second bone parts such as a first and second vertebra. The system 314 can include a pedicle screw 326 and a spinal fixation rod 325 that is secured to the pedicle screw 326. The spinal fixation rod 325 can define an inner surface 324 such as a bone facing surface and an opposed outer surface 321. The pedicle screw 326 can include a head portion 323 that defines a rod receiving channel, an engagement portion that extends from the head portion 323 and is configured to attach to bone, and a set screw 327 configured to couple to the head portion 323 so as to secure the spinal fixation rod 325 within the rod receiving channel. The head portion 323 and/or the set screw 327 can define at least one unsmooth surface 330. Therefore, it can be said that the pedicle screw and bone fixation rod are an implant body that defines at least one unsmooth surface 330. It should be appreciated, that while the spinal fixation rod 325 defines a bone facing surface that the pedicle screw can also define a bone facing surface of the system 314.

Figure 3A:
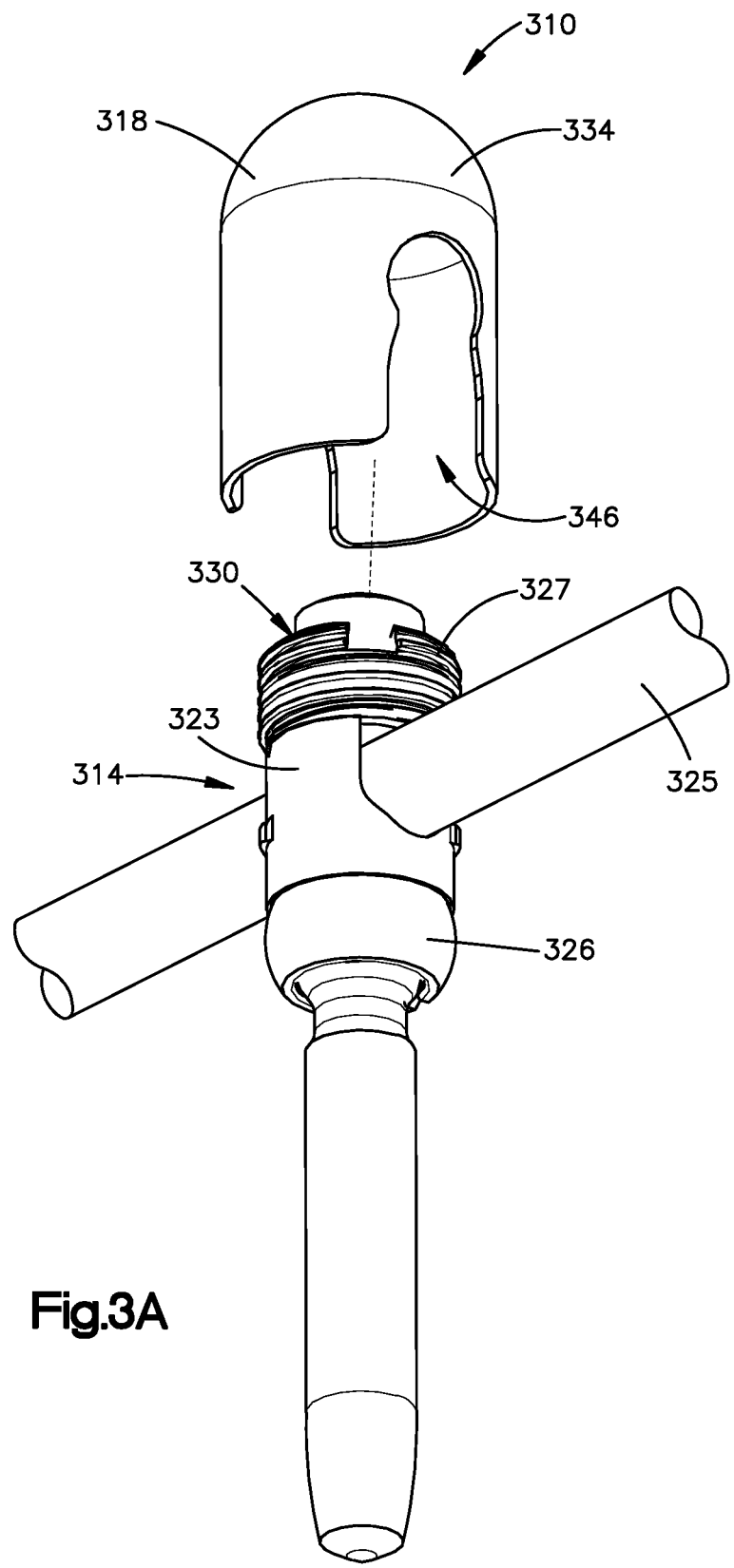
FIG. 3A is a perspective exploded view of an implant assembly that includes a spinal construct implant and a cap constructed in accordance with another embodiment, the cap being configured to couple to a spinal rod of the implant, such that the cap overlies the head of a bone screw that is coupled to the spinal rod so as to reduce sharp edges or otherwise provide smoother edges for the bone screw.

With continued reference to FIGS. 3A-3D, the cap 318 can be configured to be coupled to the system 314 and in particular to the head portion 323 of the pedicle screw 326 and/or to the spinal fixation rod 325, such that the cap 318 overlies the system 326 or at least the unsmooth surface 330 to thereby eliminate the unsmooth surface and/or reduce the palpability of the system 326. Therefore, the cap 318 can be configured to remove sharp edges from and/or reduce the palpability of the system 326 when coupled to the system 326. As shown in FIG. 3A the cap 318 includes a cap body 334 that is curved or otherwise rounded so as to reduce irritation that may be caused to the surrounding soft tissue by the system 326. The cap body 334 defines a first or upper end 338 and a second or lower end 342 that is spaced from the first end 338 along the transverse direction. The cap body 334 further includes a cavity 346 that extends into the lower end 342. The cavity 346 is configured to receive at least a portion of the system 326 such as at least a portion of the head portion 323 and/or the spinal fixation rod 325.

Figure 3D:
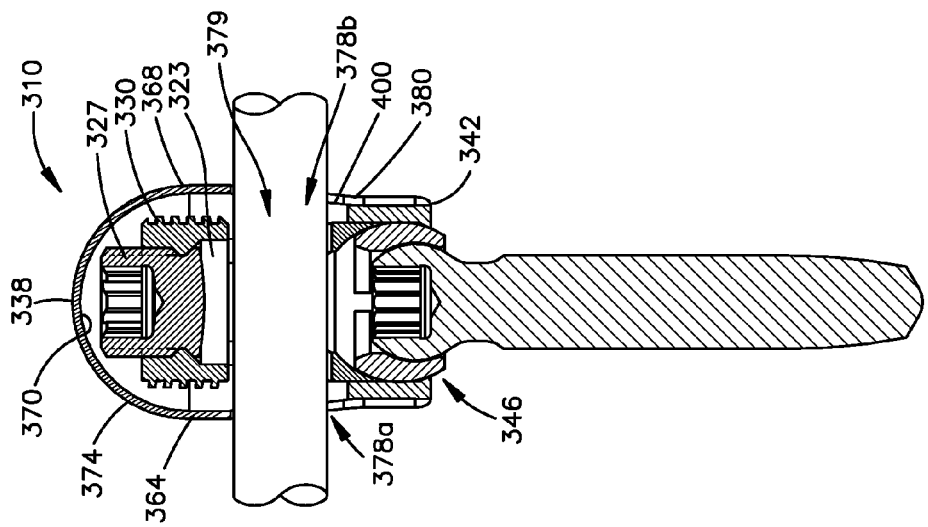
FIG. 3D is a cross-sectional view of the cap shown in FIG. 3C coupled to the spinal rod through the line 3D-3D.
Figure 3C:
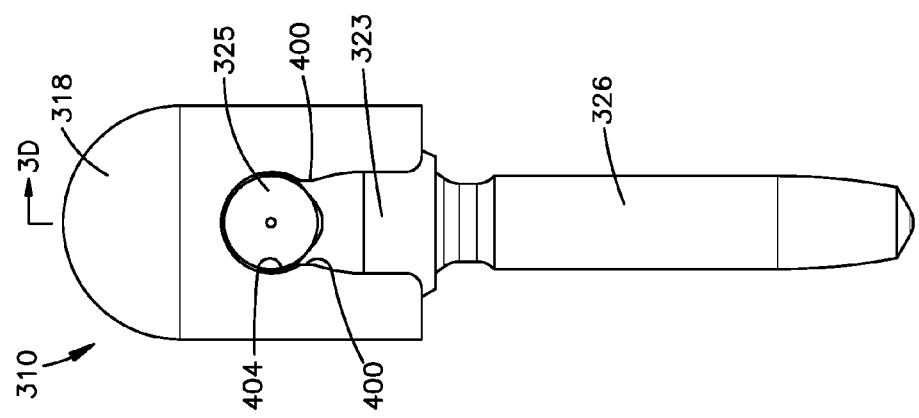
FIG. 3C is a front elevation view of the cap shown in FIG. 3B coupled to the spinal rod.

As shown in FIG. 3D, the first end 338 of the cap body 334 defines an upper surface 350 that is curved, or otherwise rounded and includes a distal body end 364 and a proximal body end 368 spaced from the distal body end 364 along the longitudinal direction L. The cap body 334 can be curved or otherwise dome shaped so as to define a convex outer surface 350. As shown in FIG. 3C, the upper surface 350 is curved such that the slope of the upper surface 350 increases as the upper surface 350 extends outward from a centerline of the upper surface 350.

As shown in FIGS. 3A-3D, the cap body 334 can define an outer shell 380 that includes a ceiling 370 and at least one side wall 374 that extends down from the first end and defines at least a first inner surface 375a and a second inner surface 375b that is spaced from and substantially faces the first inner surface 375a along a first direction (e.g. the lateral direction) such that the ceiling 370 and the first and second inner surfaces 375a and 375b at least partially define the cavity 346. In the illustrated embodiment, the outer shell 380 includes a continuous side wall 374 that is cylindrically shaped such that the first and second inner surfaces 375a and 375b are continuous with each other so as to be a single surface.

As shown in FIG. 3D, the distal end of the cap body 334 defines a first opening 378a that extends into the cavity 346 and the proximal end of the cap body 334 defines a second opening 378b that extends into the cavity 346. The cavity 346 and the first and second openings 378a and 378b together define a channel 379 that extends through the cap body 334 along a second direction (e.g. the longitudinal direction) that is substantially perpendicular to the first direction. The channel 379 is substantially cylindrically shaped and is configured to receive the spinal fixation rod 325 so as to cover a portion of the spinal fixation rod 325 and at least a portion of the head portion 323 of the pedicle screw 326 and the openings 378a and 378b are configured to allow the spinal fixation rod 325 to extend through the openings 378a and 378b when the portion of the spinal rod 325 is received within the cavity 346 or channel 379. It should be appreciated, that while the side wall 374 is continuous, the side wall 374 can be segmented, as desired.

As shown in FIG. 3C, the shell 380 is configured to elastically flex as the cavity 346 receives the head portion 323 and/or the rod 325. That is, the side wall 374 is configured to elastically flex outwardly between a first position and a second position as the cavity 346 receives the head portion 323 and/or the rod 325.

With continued reference to FIG. 3D, the cap 318 can further include an attachment mechanism that is configured to couple the cap 318 to the system 314. In the illustrated embodiment, the attachment mechanism includes at least one, such as a first and a second attachment member 400 that are configured to couple the cap 318 to the system. As shown, the attachment mechanism or each attachment member 400 can be defined by or otherwise extend from the at least one side wall substantially along the first direction. In the illustrated embodiment, the first and second attachment members 400 extend toward each other into the cavity 346 and are opposed to each other along the first direction. The attachment members 400 can each define an abutment surface 404 that faces the ceiling 370 of the cavity 346 such that when the cap 318 is coupled to the system 314 the abutment surfaces 404 abut the bone facing surface(s) 324 of the spinal fixation rod 325 to thereby trap or otherwise secure the head portion 323 and spinal fixation rod 325 within the cavity 346. It should be appreciated, that the attachment members can include other configurations. For example, the attachment members 400 can define C-clips. Moreover, it should be appreciated that the cap 318 can include features other than the attachment members 400 that are configured to couple the cap 318 to the system 314. For example, the attachment mechanism can be respective surfaces of the side walls 374 such that the surfaces create a frictional fit with the system or the attachment mechanism can be a fixation member such as a needle. Even further, the first and second attachment members 400 can be configured to abut respective bone facing surfaces of the head portion 323.

Figure 3B:
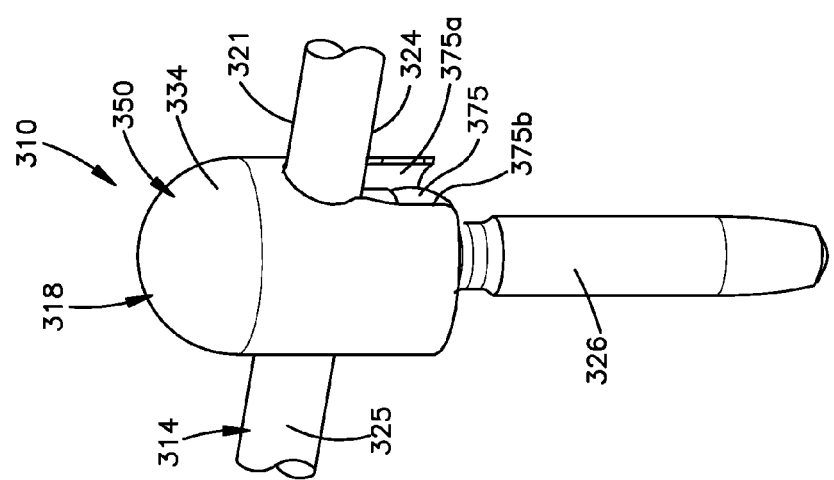
FIG. 3B is a perspective view of the cap shown in FIG. 3A coupled to the spinal rod.

In operation, a pedicle screw may be attached to a vertebra and a spinal fixation rod mad be attached to the pedicle screw to thereby form a spine fixation system 314. The cap 318 can then be coupled to the pedicle screw and/or the spinal fixation rod to thereby smooth out the sharp edges of the pedicle screw. The cap 318 can be coupled to the system 314 such that the cap 318 overlies the head portion of the pedicle screw, for example as shown in FIGS. 3B-3D.

In another embodiment and in reference to FIGS. 4A-4E, an implant assembly 410 can include an implant, illustrated as a distractor, such as a palatal distractor 414 that is configured to be coupled to at least two bone parts and a cap 418 that is configured to be coupled to the distractor 414. In particular, the distractor 414 is configured to couple to first and second bone parts so that the bone parts can be moved away from each other using the distractor 414. For example, the distractor 414 can be configured to expand an individual's maxilla. It should be appreciated, however, that the distractor 414 can be configured to expand any bone as desired.

Figure 4B:
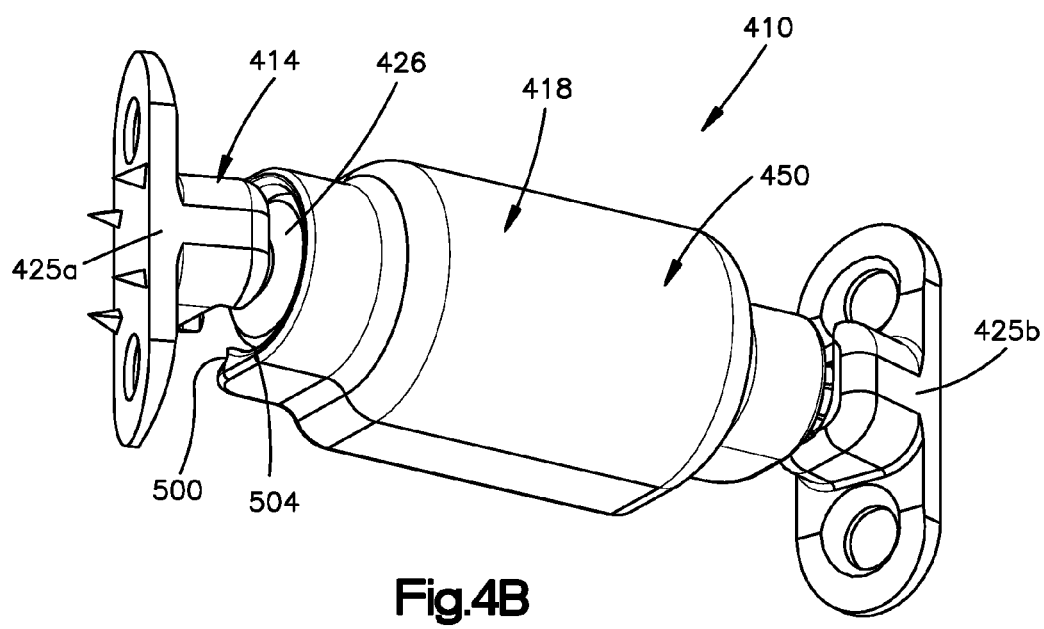
FIG. 4B is a perspective view of the cap shown in FIG. 4A coupled to the distractor.
Figure 4C:
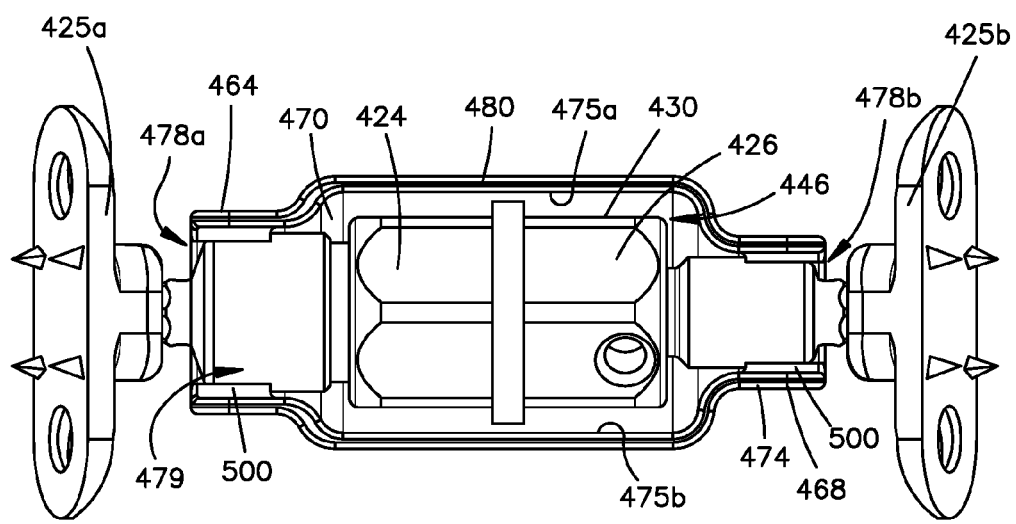
FIG. 4C is a bottom plan view of the cap shown in FIG. 4B coupled to the body.
Figure 4D:
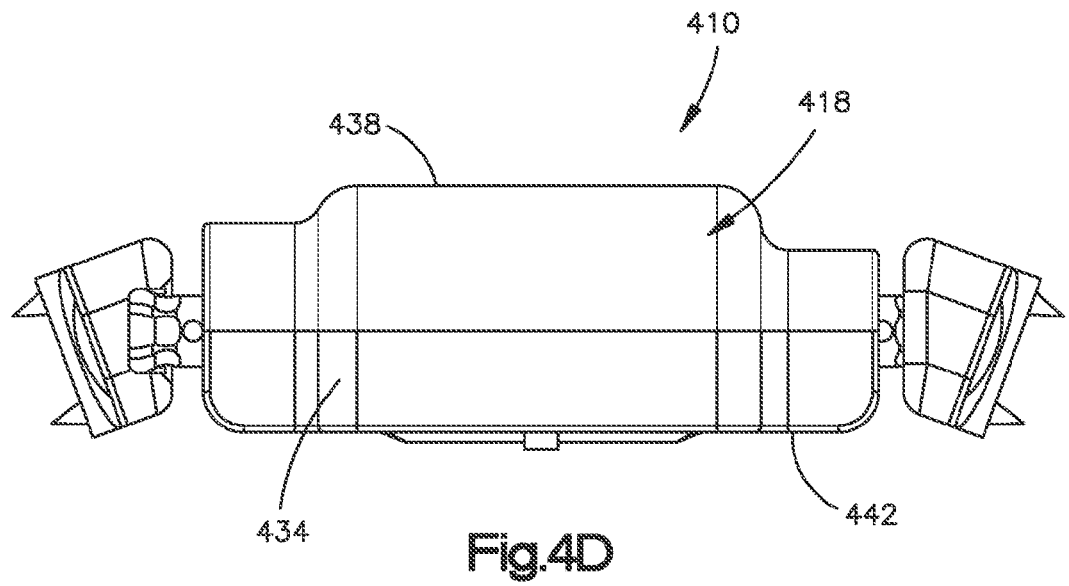
FIG. 4D is a side elevation view of the cap shown in FIG. 4B coupled to the body.

As shown in FIGS. 4A-4C, the distractor 414 can include a distractor body 426, a first coupling member 425a that extends from a first end of the distractor body 426 and a second coupling member 425b that extends from a second opposed end of the distractor body 426. The first and second coupling members 425a and 425b are configured to be attached to respective bone parts. The distractor body 426 is configured to move at least one of the first and second coupling members 425a and 425b away from the other so as to cause at least one of the bone parts to move away from the other. The distractor body 426 can define an inner surface 424 such as a tissue facing surface and an opposed outer surface 425. The distractor body 426 can further define at least one unsmooth surface 430.

With continued reference to FIGS. 4A-4E, the cap 418 can be configured to be coupled to the distractor 414 and in particular to the distractor body 426, such that the cap 418 overlies the distractor body 426 or at least the unsmooth surface 430 to thereby eliminate the unsmooth surface and/or reduce the palpability of the distractor body 426. Therefore, the cap 418 can be configured to remove sharp edges from and/or reduce the palpability of the distractor body 426 when coupled to the distractor body 426. As shown in FIGS. 4A and 4B the cap 418 includes a cap body 434 that is curved or otherwise rounded so as to reduce irritation that may be caused to the surrounding soft tissue (e.g. a tongue) by the distractor body 426. The cap body 434 defines a first or upper end 438 and a second or lower end 442 that is spaced from the first end 438 along the transverse direction. The cap body 434 further includes a cavity 446 that extends into the lower end 442. The cavity 446 is configured to receive at least a portion of the distractor body 426.

Figure 4E:
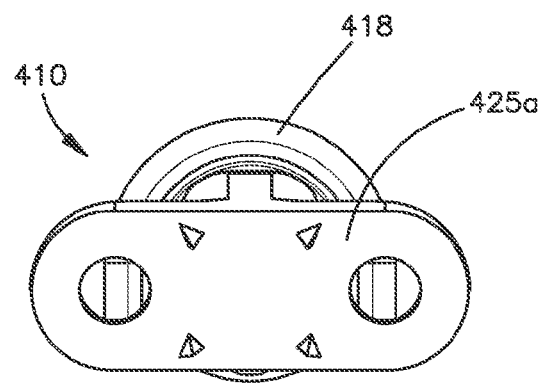
FIG. 4E is a front elevation view of the cap shown in FIG. 4B coupled to the body.

As shown in FIG. 4B, the first end 438 of the cap body 434 defines an upper surface 450 that is curved, or otherwise rounded and includes a distal body end 464 and a proximal body end 468 spaced from the distal body end 464 along the longitudinal direction L. The cap body 434 can be curved or otherwise rounded along the lateral direction so as to define a convex outer surface 450. As shown in FIG. 4E, the upper surface 450 is curved such that the slope of the upper surface 450 increases as the upper surface 450 extends outward from a centerline of the upper surface 450.

As shown in FIGS. 4B-4E, the cap body 434 can define an outer shell 480 that includes a ceiling 470 and at least one side wall 474 that extends from the first end 438 and defines at least a first inner surface 475a and a second inner surface 475b that is spaced from and substantially faces the first inner surface 475a along a first direction (e.g. the lateral direction) such that the ceiling 470 and the first and second inner surfaces 475a and 475b at least partially define the cavity 446. In the illustrated embodiment, the outer shell 480 includes first and second side walls 474 that are parallel to each other and opposed to each other along the first direction such that the first and second inner surfaces 475a and 475b are parallel to each other and opposed to each other along the first direction.

As shown in FIG. 4C, the distal end of the cap body 434 defines a first opening 478a that extends into the cavity 446 and the proximal end of the cap body 434 defines a second opening 478b that extends into the cavity 446. The cavity 446 and the first and second openings 478a and 478b together define a channel 479 that extends through the cap body 434 along a second direction (e.g. the longitudinal direction) that is substantially perpendicular to the first direction. The channel 479 is substantially cylindrically shaped and is configured to receive the distractor body 426 so as to cover a portion of the distractor body 426 and the openings 478a and 478b are configured to allow the first and second coupling members 425a and 425b to extend through the openings 478a and 478b when the portion of the distractor body 426 is received within the cavity 446 or channel 479.

As shown in FIG. 4C, the shell 480 is configured to elastically flex as the cavity 446 receives the distractor body 426. That is, the side walls 474 are configured to elastically flex outwardly between a first position and a second position as the cavity 446 receives the distractor body 426.

With continued reference to FIG. 4C, the cap 418 can further include an attachment mechanism that is configured to couple the cap 418 to the distractor 414. In the illustrated embodiment, the attachment mechanism includes at least one, such as first, second, third, and fourth attachment members 500 that are configured to couple the cap 418 to the distractor. As shown, the attachment mechanism or each attachment member 500 can be defined by or otherwise extend from the at least one side wall substantially along the first direction. In the illustrated embodiment, the first and second, and the third and fourth attachment members 500 extend toward each other into the cavity 446 and are opposed to each other along the first direction. The attachment members 500 can each define an abutment surface 504 that faces the ceiling 470 of the cavity 446 such that when the cap 418 is coupled to the distractor 414 the abutment surfaces 504 abut the inner surface(s) 424 of the distractor body 426 to thereby trap or otherwise secure the distractor body 426 within the cavity 446. It should be appreciated, that the attachment members can include other configurations. For example, the attachment members 500 can define C-clips. Moreover, it should be appreciated that the cap 418 can include features other than the attachment members 500 that are configured to couple the cap 418 to the distractor 414. For example, the attachment mechanism can be respective surfaces of the side walls 474 such that the surfaces create a frictional fit with the system or the attachment mechanism can be a fixation member such as a needle. Even further, the first and second attachment members 500 can be configured to abut respective inner surfaces of the distractor body 426.

In operation, a distractor 414 may be attached to a pair of palatal bone portions. The cap 418 can then be coupled to the distractor 414 to thereby smooth out the sharp edges of the distractor 414. The cap 418 can be coupled to the distractor 414 such that the cap 418 overlies the distractor body 426, for example as shown in FIGS. 4B-4E.

In another embodiment and in reference to FIGS. 5A and 5B, an implant assembly 510 can include a cap 518 that is configured to be coupled to an aperture 519 defined by an anatomical structure 520 such as a clamp member of a cranial clamp as illustrated. In particular the cap 518 can be configured to be coupled to the implant 520 through an aperture 519, such that the cap 518 overlies the aperture 519 or at least an unsmooth surface of the implant 520 to thereby eliminate the unsmooth surface and/or reduce the palpability of the implant. Therefore, the cap 518 can be configured to remove sharp edges from and/or reduce the palpability of the implant when coupled to the implant. As shown in FIG. 5B the cap 518 includes a cap body 534 that is curved or otherwise rounded so as to correspond to the curved surface of the implant 520 and thereby reduce irritation that may be caused to the surrounding soft tissue by the implant 520. The cap body 534 defines a first or upper end 538 and a second or lower end 542 that is spaced from the first end 538 along the transverse direction. It should be appreciated that the cap 518 can be further configured to couple to an aperture defined by a bone such that the cap 518 overlies the bone when coupled to the bone. For example, cap 518 can be configured to engage an aperture defined by the bone to thereby couple the cap 518 to the bone.

As shown in FIG. 5B, the first end 538 of the cap body 534 defines an upper surface 550 that is curved, or otherwise rounded so as to define a convex outer surface 550. The cap body 534 can define an outer shell 580 and an inner shell 584 disposed within the outer shell 580. The outer shell 580 includes a ceiling 570 that substantially corresponds to the outer surface of the implant 520 and the inner shell 584 includes at least one side wall 574 that define at least a first inner surface 575a and a second inner surface 575b that is spaced from and substantially faces the first inner surface 575a along a first direction (e.g. the lateral direction). As shown in FIG. 5B, the inner shell 584 can further define an outer surface 596. Because the inner surfaces 575a and 575b are spaced from each other, the inner shell 584 is configured to elastically flex relative to the outer shell 580 when the inner shell 584 is received by the aperture 519. That is, the at least one side wall 574 of the inner shell 584 is configured to elastically flex inwardly between a first position and a second position as the inner shell 584 is received by the aperture 519. It should be appreciated, however, that the inner shell 584 can be configured to be non-flexible, as desired.

The inner shell 584 or at least the at least one side wall 574 can be configured to be inserted through one of the apertures of the implant 520 or into the aperture of the bone. In the illustrated embodiment, the at least one side wall 574 is substantially continuous and is substantially cylindrical in shape. It should be appreciated, however, that the at least one side wall 574 is discontinuous and/or has a different shape as desired, so long as the inner shell 584 can be passed through a aperture in the implant or bone.

With continued reference to FIG. 5B, the cap 518 can further include an attachment mechanism that is configured to couple the cap 518 to the implant or bone. In the illustrated embodiment, the attachment mechanism includes at least one, such as a first and a second attachment member 600 that are configured to couple the cap 518 to the implant or bone. As shown, the attachment mechanism or attachment members 600 can be defined by or otherwise extend from the at least one side wall and can be substantially continuous as the attachment member extends around the side wall. Therefore, it can be said that at least a portion of the at least one attachment member 600 extends away from another at least a portion of the at least one attachment member 600 and the at least a portions of the attachment member 600 are opposed to each other along the first direction. The attachment member 600 can be configured to provide an interference fit with the implant 520 when the inner shell 584 is received by the aperture 519 as illustrated in FIG. 5B. It should be appreciated, however, that the attachment member 600 can be configured to define an abutment surface that is configured to abut an inner surface of the implant 520. Further it should be appreciated that the attachment mechanism can be an external surface of the side wall 574 such that the external surface creates a frictional fit with the bone or implant.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

What is claimed:

1. A cap configured to be coupled to an implant, the cap comprising:
    a cap body that includes a shell having at least one side wall, the at least one side wall defining at least a first inner surface and a second inner surface that is spaced from the first inner surface along a first direction such that the second inner surface substantially faces the first inner surface, the cap body further including a cavity that is sized to receive at least a portion of the implant such that the shell elastically flexes between a first position and a second position as the cavity receives the at least a portion of the implant, the first inner surface and the second inner surface each partially defining the cavity; and
    an attachment mechanism defined by the at least one side wall, the attachment mechanism including a first attachment member and a second attachment member, the first and second attachment member each extending from the at least one side wall substantially along the first direction,
    wherein the attachment mechanism is configured to capture the at least a portion of the implant within the cavity when the shell is in the second position.

2. The cap of claim 1, wherein the first and second attachment members are configured to abut respective bone facing surfaces of the implant when the at least a portion of the implant is captured within the cavity.

3. The cap of claim 1, wherein the first and second attachment members are opposed to each other along the first direction.

4. The cap of claim 1, wherein the first and second attachment members extend toward each other substantially along the first direction.

5. The cap of claim 1, wherein the at least one side wall defines a third surface that joins the first surface to the second surface.

6. The cap of claim 5, wherein the first, second, and third surfaces are continuous.

7. The cap of claim 1, wherein the shell defines the cavity.

8. The cap of claim 7, wherein the cap body further includes an outer shell that defines an inner surface, wherein the shell is an inner shell that further defines an outer surface that faces and is spaced apart from the inner surface of the outer shell such that the inner shell is configured to flex outwardly toward the outer shell as the cavity receives the at least a portion of the implant.

9. The cap of claim 1, wherein the cap body defines an outer surface that is at least partially convex.

10. The cap of claim 1, wherein the shell includes a ceiling that partially defines the cavity, and each of the first and second attachment members defines an abutment surface that at least partially faces the ceiling.

11. The cap of claim 1, wherein the cap body defines a first opening that extends into the cavity such that a portion of the implant extends through the opening when the at least a portion of the implant is received by the cavity.

12. The cap of claim 1, wherein the shell defines the cavity and the cap body defines first and second openings that extend into the cavity such that the cavity and first and second openings define a channel that extends through the cap body along a second direction that is substantially perpendicular to the first direction.

13. The cap of claim 12, wherein the at least one side wall includes a first side wall and a second side wall that is spaced from the first side wall along the first direction.

14. The cap of claim 12, wherein the channel is at least partially cylindrical in shape.

15. The cap of claim 1, wherein the cap body further includes an outer shell and the shell is an inner shell, the outer shell defining the cavity and the inner shell being configured to flex such that the first and second surfaces move toward each other as the cavity receives the at least a portion of the implant.

16. The cap of claim 15, wherein the inner shell is sized to be received by an aperture defined by the implant.

17. The cap of claim 16, wherein the attachment mechanism is an external surface of the at least one side wall such that the external surface is configured to form a frictional fit with the implant when the inner shell is inserted into the aperture.

18. The cap of claim 16, wherein the at least one side wall is cylindrical such that the first and second inner surfaces are continuous so as to define a single cylindrical surface.

19. The cap of claim 1, wherein the cap body includes a first end and a second end, the cavity extending into the second end toward the first end, the at least one side wall extend from the first end such that the at least one side wall is flexible relative to the first end.

20. A method of fixing a first bone part relative to a second bone part, the method comprising:
    fixing a first bone part relative to a second bone part with an implant that defines a bone facing surface and an opposed outer surface;
    positioning a cap defining a curved outer surface over the outer surface of the implant, the cap having an inner shell that defines a cavity, an outer shell, and at least one attachment member that extends from the inner shell; and
    moving the cap toward the implant such that the cavity receives a portion of the implant, thereby flexing the inner shell relative to the outer shell, and moving the cap toward the implant until the at least one attachment member abuts the bone facing surface to thereby couple the cap to the implant.

21. The method of claim 20, further comprising the step of inserting a portion of the implant through an opening of the cap body that extends into cavity.

22. The method of claim 20, further comprising the step of moving the cap toward the implant until a ceiling of the inner shell abuts the implant, the ceiling facing the first and second attachment members prior to the step of moving the cap toward the implant.

23. The cap of claim 1, wherein the first attachment member extends from the first inner surface, and the second attachment member extends from the second inner surface.

24. A cap configured to be coupled to an implant, the cap comprising:
- a cap body including an inner shell and an outer shell, the inner shell having at least one side wall, the at least one side wall defining at least a first inner surface and a second inner surface that is spaced from the first inner surface along a first direction such that the second inner surface substantially faces the first inner surface, the inner shell including an outer surface, the outer shell including an inner surface that faces the outer surface, the cap body further including a cavity that is defined by the inner shell, and the cavity is sized to receive at least a portion of the implant such that the inner shell is configured to elastically flex: 1) between a first position and a second position as the cavity receives the at least a portion of the implant, and 2) outwardly toward the outer shell as the cavity receives the at least a portion of the implant; and
- an attachment mechanism defined by the at least one side wall, the attachment mechanism including a first attachment member and a second attachment member, the first and second attachment member each extending from the at least one side wall substantially along the first direction,
- wherein the attachment mechanism is configured to capture the at least a portion of the implant within the cavity when the inner shell is in the second position.

25. The cap of claim 24, wherein the outer surface is at least partially convex.

26. The cap of claim 24, wherein the inner shell includes a ceiling that partially defines the cavity, and each of the first and second attachment members defines an abutment surface that at least partially faces the ceiling.

27. The cap of claim 24, wherein the cap body defines a first opening that extends into the cavity such that a portion of the implant extends through the opening when the at least a portion of the implant is received by the cavity.

28. A cap configured to be coupled to an implant, the cap comprising:
- a cap body that includes a shell having at least one side wall, the at least one side wall defining at least a first inner surface and a second inner surface that is spaced from the first inner surface along a first direction such that the second inner surface substantially faces the first inner surface, the cap body further including a cavity that is sized to receive at least a portion of the implant such that the shell elastically flexes between a first position and a second position as the cavity receives the at least a portion of the implant, the shell including a ceiling that partially defines the cavity; and
- an attachment mechanism defined by the at least one side wall, the attachment mechanism including a first attachment member and a second attachment member, the first and second attachment member each extending from the at least one side wall substantially along the first direction such that each of the first and second attachment members define respective abutment surfaces that at least partially face the ceiling,
- wherein the attachment mechanism is configured to capture the at least a portion of the implant within the cavity when the shell is in the second position.

29. The cap of claim 28, wherein the outer surface is at least partially convex.

30. The cap of claim 28, wherein the cap body defines a first opening that extends into the cavity such that a portion of the implant extends through the opening when the at least a portion of the implant is received by the cavity.

* * * * *